United States Patent
Nakazeki et al.

[11] Patent Number: 6,129,660
[45] Date of Patent: *Oct. 10, 2000

[54] METHOD OF CONTROLLING BLOOD PUMP

[75] Inventors: Tsugito Nakazeki, Shizuoka; Teruaki Akamatsu, Kyoto; Toshihiko Nojiri, Kanagawa, all of Japan

[73] Assignee: NTN Corporation, Osaka, Japan

[*] Notice: This patent is subject to a terminal disclaimer.

[21] Appl. No.: 09/013,218

[22] Filed: Jan. 26, 1998

Related U.S. Application Data

[63] Continuation-in-part of application No. 08/697,235, Aug. 21, 1996, abandoned.

[30] Foreign Application Priority Data

Aug. 23, 1995 [JP] Japan ................................. 7-214760

[51] Int. Cl.[7] .................................................. A61M 1/10
[52] U.S. Cl. .................................. 600/17; 623/3; 415/900
[58] Field of Search ............................ 600/16, 17; 623/3; 415/900

[56] References Cited

U.S. PATENT DOCUMENTS

| | | |
|---|---|---|
| 4,763,032 | 8/1988 | Bramm et al. . |
| 4,781,716 | 11/1988 | Richelsoph . |
| 4,944,748 | 7/1990 | Bramm et al. . |
| 5,055,005 | 10/1991 | Kletschka . |
| 5,064,353 | 11/1991 | Tsukahara . |
| 5,112,202 | 5/1992 | Oshima et al. ........................ 415/900 |
| 5,527,159 | 6/1996 | Bozeman, Jr. et al. ............... 415/900 |
| 5,711,753 | 1/1998 | Pacella et al. ............................ 600/16 |
| 5,725,357 | 3/1998 | Nakazeki et al. ...................... 415/900 |

FOREIGN PATENT DOCUMENTS

91/01584  2/1991  WIPO ................................. 415/900

OTHER PUBLICATIONS

Nishimura et al, "Control of the Pressure Flow Relationship With a Magnetically Suspended Centrifugal Pump in a Chronic Animal Experiment", ASAIO Journal, 1997, M553–M556.

*Primary Examiner*—George R. Evanisko
*Attorney, Agent, or Firm*—McDermott, Will & Emery

[57] ABSTRACT

When a current is set, a PI control portion performs proportional integration control, a power amplifying circuit performs power amplification, whereby a current flowing through a motor is controlled to have a constant value. Further, the changes of the number of rotation is positively feedback and the changes are added to the set current by an adder. Further, blood viscosity is detected by a viscosity detecting circuit, an amount of correction is calculated by a correcting amount operating circuit so that it becomes equal to a reference value, and the calculated correcting amount is added to the adder.

10 Claims, 6 Drawing Sheets

| Kp | PROPORTIONAL GAIN | L | COIL CONDUCTANCE | Kt | TORQUE CONSTANT |
| Ki | INTEGRATION GAIN | R | COIL RESISTANCE | Ke | BACK ELECTROMOTIVE FORCE CONSTANT |
| J | MOMENT OF INERTIA | I | MOTOR CURRENT | | |
| N | SPEED OF ROTATION | K | SPEED POSITIVE FEEDBACK GAIN | V | VOLTAGE APPLIED TO MOTOR |
| | | | | N(Q)n | LOAD TORQUE CONSTANT |

PRESSURE

FLOW RATE

METHOD OF CONTROLLING BLOOD PUMP

This application is a continuation-in-part of application Ser. No. 08/697,235 filed Aug. 21, 1996, now abandoned.

BACKGROUND OF THE INVENTION

1. Field of the Invention

The present invention relates to a method of controlling a blood pump. More specifically, the present invention relates to a method of controlling a blood pump used for medical equipment such as an artificial heart and an artificial heart-lung in which an impeller is supported by a magnetic bearing.

2. Description of the Background Art

A turbo pump such as a centrifugal pump or an axial flow pump, can be adapted to have higher performance and be smaller in size than a pulsatile type pump. Hence, the turbo pump has come to be used, for example, as a blood pump for an artificial heart. Flow rate in a turbo pump is generally controlled by changing the rotation speed of the pump.

FIG. 7 shows flow-pressure characteristic of a centrifugal pump. As shown by the solid line curve in FIG. 7, pressure in a typical prior art centrifugal pump hardly changes when the maximum flow rate only reaches a medium level.

FIG. 8 shows an exemplary use of the blood pump in which bypasses 2 and 3 are provided for a natural heart, and blood pump 4 assists the heart after surgical operation. Blood from lung 7 is supplied to blood pump 4 through bypass 3, and returned to aorta 15, pressurized by blood pump 4. The blood flows from aorta 15 through capillary vessel 5 and 6 to right atrium 13, from right atrium 13 to right ventricle 14, from right ventricle 14 to lung 7 and returns to left atrium 12.

In this case, flow rate of the pump depends on the discharge pressure of natural heart 1 and on fluctuation of pressure load caused by the variation in cannula resistance of the blood vessel. Reduction in pump flow rate causes thrombus in the pump, while excessive flow rate affects the organ. In order to suppress variation in the flow rate and achieve the desired characteristics as plotted by the dotted line in FIG. 7, it may be possible to make the tube narrower. However, in that case, pump efficiency degrades naturally. Such problem can be eliminated by realizing the characteristic represented by the straight line A in FIG. 7 having a constant inclination.

SUMMARY OF THE INVENTION

Therefore, an object of the present invention is to provide a method of controlling a blood pump in which change in flow rate of the blood pump with respect to fluctuation of pressure load can be suppressed.

Briefly stated, the present invention is directed to a method of controlling a blood pump for assisting or totally displacing a natural heart bypass connection, which controls a current flowing through a motor for driving the blood pump so that it is kept constant.

Therefore, according to the present invention, change in the flow rate of the blood pump with respect to the fluctuation in pressure load can be effectively suppressed.

According to another aspect, the current flowing through the motor for driving the blood pump is controlled to be constant, and the speed is positively feedback and added to a current instruction value.

Therefore, according to the present invention, ideal pump characteristics can be obtained by adjusting the positive feedback gain.

Preferably, the blood pump is controlled by an analog circuit, whereby risk of malfunction experienced in software processing can be avoided.

Preferably, blood viscosity is detected and compared with a reference value, an amount of correction is calculated, and the correcting value is added to the current instruction value of the motor, whereby accuracy in flow rate control can be improved.

Preferably, the blood pump includes an impeller, which impeller is supported by a magnetic bearing arrangement, and the impeller is rotated by a motor through the magnetic coupling. The magnetic bearing arrangement may include a first magnetic bearing supporting one side of the impeller and a second magnetic bearing supporting another side of the impeller.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
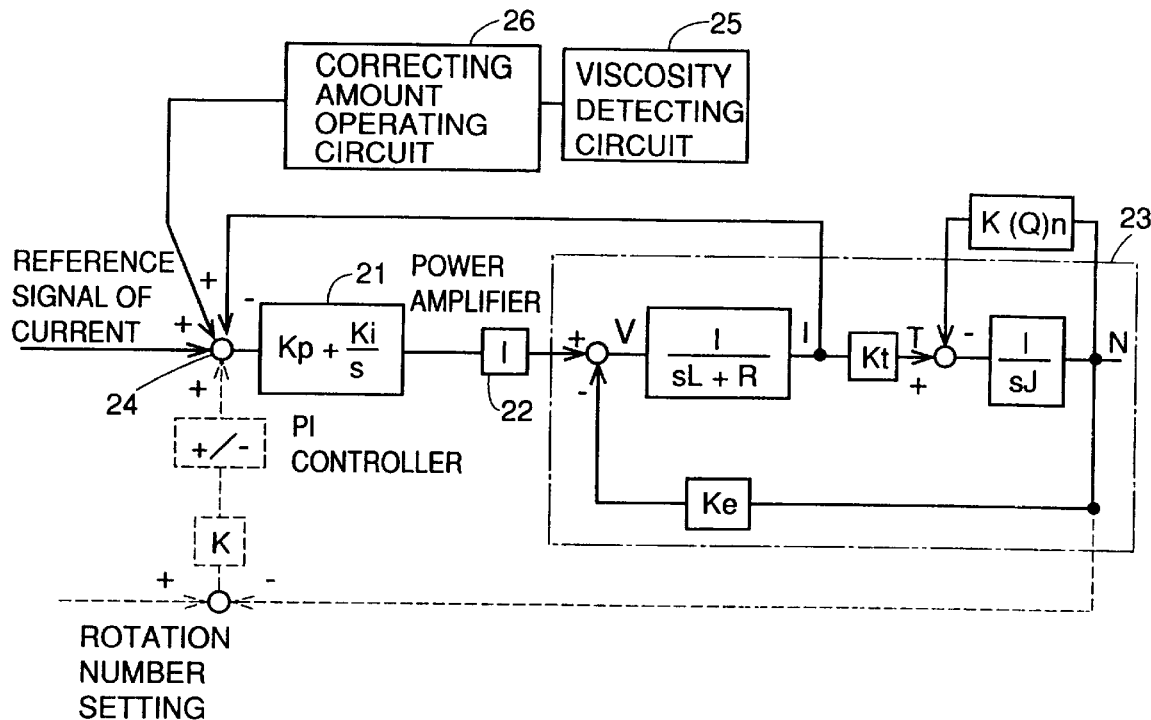
FIG. 1 is a block diagram of motor control showing an embodiment of the present invention.

FIG. 1 is a block diagram of exemplifying a motor control scheme embodiment of the present invention. Block 23, surrounded by a chain dotted line, represents transfer functions of a DC servo motor in the form of a block diagram. This transfer function format is a common shorthand, long well-known in the art, for representing motor feedback control circuit functionality. Block diagram representation of transfer functions is indicative to the artisan of circuitry necessary to perform the transfer function operations, as may be seen, for example, in the Engineering Handbook, "DC Motors, Speed Controls, Servo Systems," 3rd Edition, Electro-Craft Corporation, October, 1975, wherein transfer function representations are shown at pp. 4-17, 4-26 and 4-35.

In the arrangement shown in FIG. 1, when a current for driving the motor is set, a PI control portion 21 performs proportional integral control and, based on an output therefrom, a power amplifying circuit 22 performs power amplification, so that the servo motor represented by the block 23 is driven. In block 23, the expression $1/(sL+R)$ represents conversion of a voltage to a current, Kt represents conversion of the current to torque T, 1/sJ represents dynamic characteristic of a rotor and Ke represents a back electromotive force constant. The conversion of the voltage to a current is fed back to the adder, 24, and compared with the reference current to maintain the current at the reference current to control the motor.

A pump load torque is represented as the speed N multiplied by a load torque constant K(Q)n. Especially in a magnetic suspension type, generation of a thrombus is not likely as there is no contact portion and, therefore, the load torque constant K(Q)n can be maintained stable for a long period of time. Here, torque K(Q)n is a function of flow rate Q. In a steady state where the current is controlled to have a constant value, a constant torque proportional to the motor current acts on the pump, and the motor rotates at a speed which satisfies the relation T=K(Q)n•N. When the cannula resistance of the cardiovascular system or the system distributing the blood increases incrementally, load torque decreases as the flow rate decreases. With the current controlled to be constant (constant torque) the speed increases until the load torque matches the driving torque. When the cannula resistance decreases, the operation is reversed.

Figure 2:
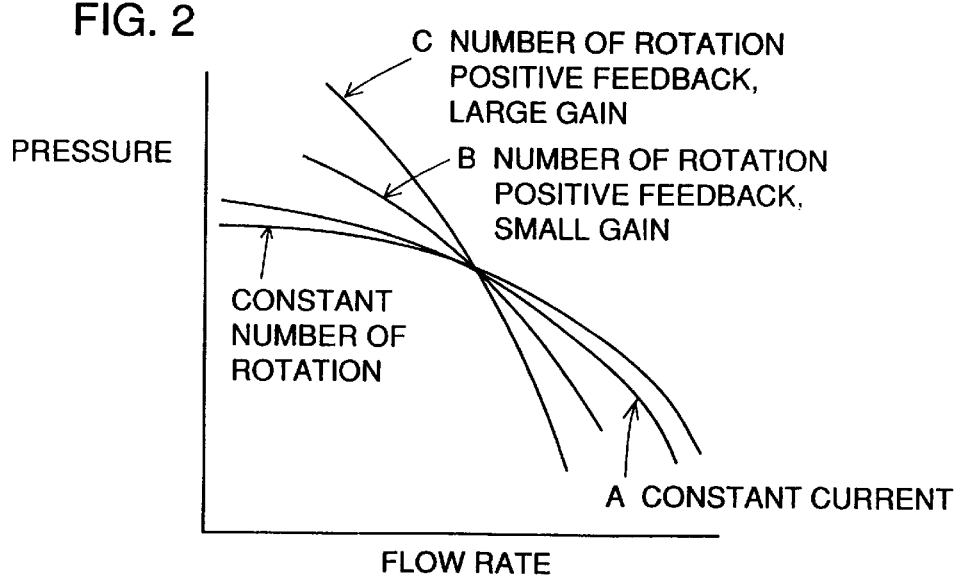
FIG. 2 shows the flow rate-pressure characteristic of a centrifugal pump.

FIG. 2 shows flow-rate pressure characteristics of the centrifugal pump. The curve A of FIG. 2 represents the relation between the flow rate and the pressure where current is constant, which has larger inclination than the curve where the speed is constant.

The function of positive speed feedback represented by the dotted line in FIG. 1 is as follows. The increase in speed due to the increase in cannula resistance is added to the reference current value by an adder 24 through the loop plotted in the dotted line, and the motor current increases. Therefore, the speed further increases until it is balanced with the load torque. If the positive feedback gain is too large, the control system becomes instable. Curves B and C shown in FIG. 2 correspond to characteristics with positive feedback. By adjusting the positive feedback gain, an arbitrary characteristic can be obtained, and the flow rate-pressure characteristic which corresponds to the line A having a prescribed inclination shown in FIG. 5 can be realized.

In FIG. 1, a viscosity detecting circuit 25 detects viscosity of the blood. Viscosity detection is based on the following characteristics of blood. Blood contains blood cells (hemocytes), made up of red blood cells (hematids) and white blood cells (leukocytes), and plasma, which includes fibrin and serum. Blood viscosity is roughly proportional to the ratio of blood cell volume to total blood volume, which is referred to as hematocrit value. Blood viscosity generally can be found by obtaining the hematocrit value by blood analysis. In order to measure the hematocrit value in the current invention, means for directing light to blood flowing through a blood pump may be provided, for example, and light transmission may be measured by a sensor. While a coefficient of conversion from the hematocrit value to the viscosity may differ when the blood contains excessive fat, for example, accurate conversion is possible by preliminary calibration. Alternatively, the blood viscosity may be found by measuring blood flow rate by drawing blood to a capillary, utilizing Bernoulli's law, as blood is liquid.

The detected viscosity data is compared with a reference blood viscosity level, an amount of correction for making constant the flow rate is calculated by a correcting amount operating circuit 26, and it is added to the reference current value by adder 24. These series of control circuits each can be implemented by conventional analog circuitry.

Figure 3:
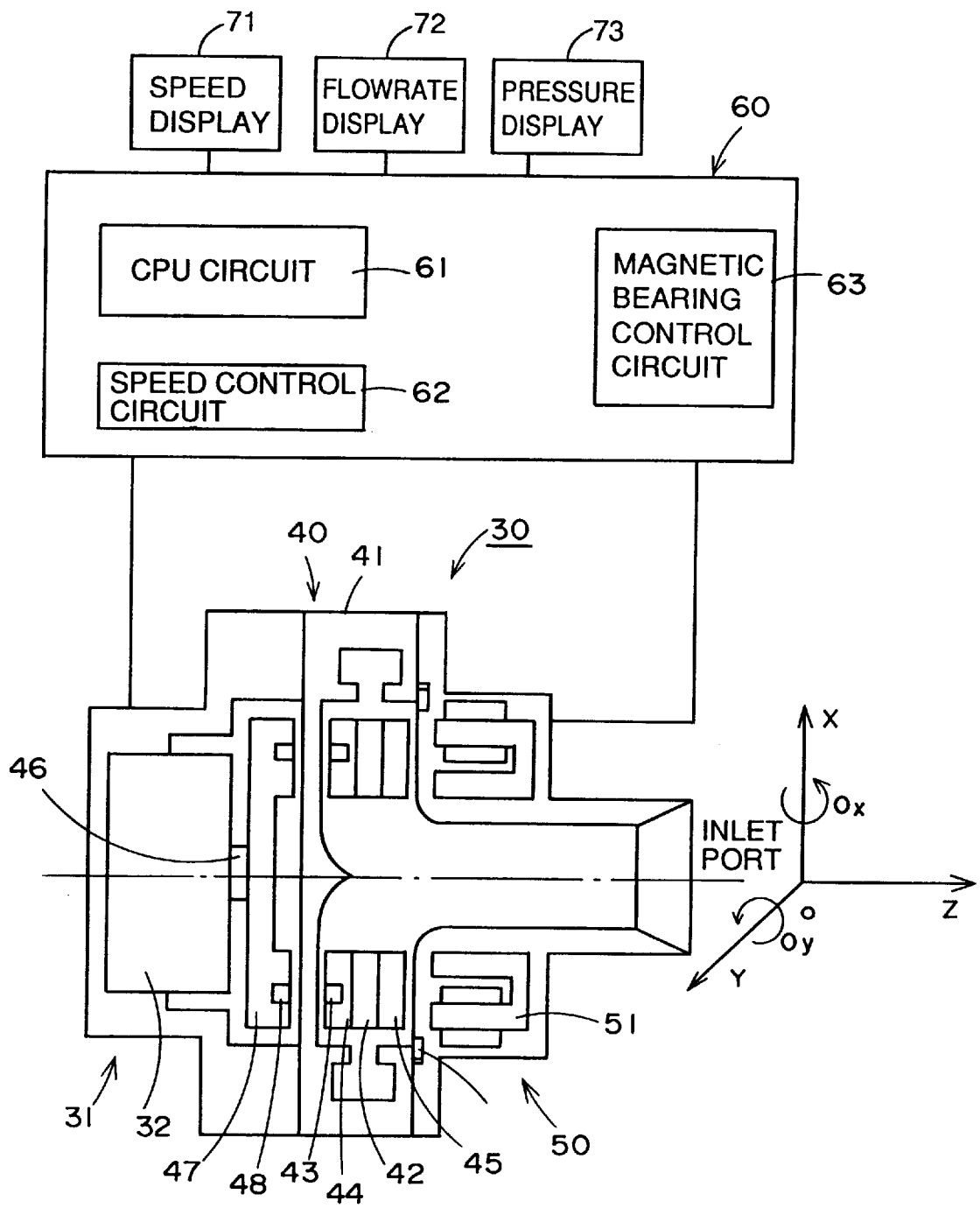
FIG. 3 shows a magnetically suspended pump and control circuit thereof, to which the present invention is applied.

FIG. 3 shows a magnetic suspension type pump and control circuit thereof in accordance with the present invention. A magnetic suspension type pump 30 includes a motor portion 31, a pump portion 40 and a magnetic bearing portion 50. In a casing 41 of pump portion 40, there is provided an impeller 42. Casing 41 is formed of a non-magnetic material. Impeller 42 includes a non-magnetic member 44 containing a permanent magnet 43, which forms a passive magnetic bearing, and a soft iron 45 that forms a rotor of an active magnetic bearing. Permanent magnet 43 is divided along the circumferential direction of impeller 42, and magnets adjacent to each other are magnetized in mutually opposite directions.

Outside the casing 41, a rotor 47, axially supported by a shaft 46, is provided opposing the side of impeller 42 which has permanent magnets 43. Rotor 47 is driven by motor 32 to rotate. Rotor 47, provided with permanent magnets 48, has the same number of permanent magnets as impeller 42 so that attracting forces act therebetween. An electromagnet 51 and a position sensor, not shown, are provided in magnetic bearing portion 50 opposite from the side of impeller 42 which has soft iron 45, such that impeller 42 is held at the center of casing 41 by attracting force between permanent magnets 43 and 48 in casing 41.

In the magnetic suspension type pump structured as described above, permanent magnet 43 buried in rotor 47 supports the impeller in the radial direction and drives impeller 42, generating attracting force in the axial direction with the permanent magnet 43 provided on impeller 42. A current is caused to flow through the coil of electromagnet 51 to be balanced with the attracting force, and impeller 42 floats. When rotor 47 rotates by the driving force of motor 31, impeller 42 rotates by magnetic coupling between permanent magnets 43 and 48, and the blood is discharged from inlet port to an outlet port, not shown. Since impeller 42 is separated from rotor 47 by means of casing 41, the blood is not contaminated by electromagnet 51, and the blood discharged from magnetic suspension type pump 30 is kept clean.

Control circuit 60 includes a CPU circuit 61, a speed control circuit 62, and a magnetic bearing control circuit 63. An exemplified embodiment of speed control circuit 62 is shown in FIG. 1. The speed of motor 31 is controlled by an instruction from CPU circuit 61, and the current of magnet 51 is controlled by magnetic bearing control circuit 63 based on a signal received from a position sensor. Control portion 60 additionally is provided with a display 71 for displaying the speed of rotation, a display 71 for displaying flow rate, and a display 73 for displaying pressure are provided, as needed.

Figure 4:
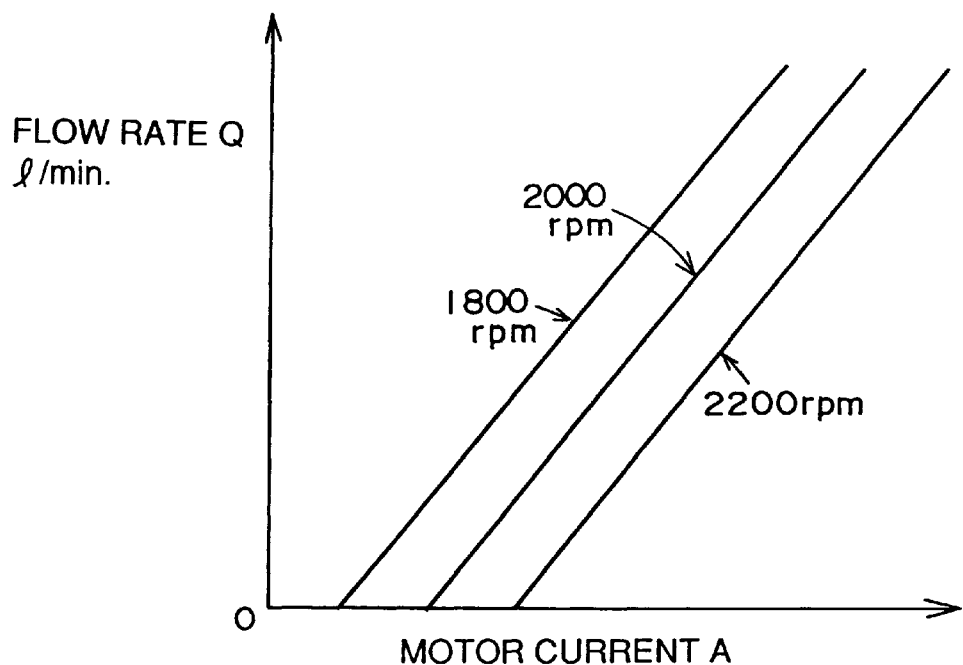
FIG. 4 shows the relation between the discharge flow rate of the magnetically suspended pump shown in FIG. 3 and driving current of the motor, for various speeds.
Figure 5:
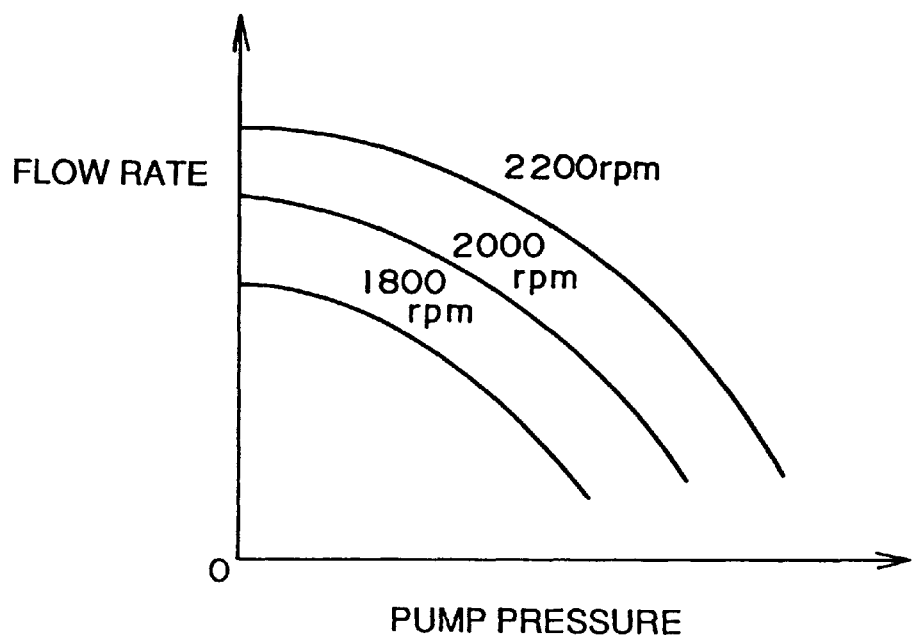
FIG. 5 shows pump discharge flow rate-pressure characteristics at different speeds.

FIG. 4 shows the relation between the discharge flow rate of the magnetic suspension type pump and driving current of the motor for various speeds. FIG. 5 shows pump discharge flow rate-pressure characteristic at each speed. The characteristics of the magnetic suspension type pump shown in FIG. 2 change dependent on the gap between casing 41 and impeller 42 and on viscosity of the fluid. However, by previous determination for each pump, the discharge flow rate can be obtained easily based on the motor driving current and the speed, as shown in FIG. 4. Further, based on the characteristics shown in FIG. 5, the discharge pressure can be calculated based on the flow rate and the speed.

Referring to FIGS. 3 to 5, a specific operation of one embodiment of the present invention will be described. By the speed control circuit 62 of control circuit 60, a constant current is supplied to motor 32, and based on the characteristic shown in FIG. 4, the current can be calculated using the speed and the motor driving current. If impeller 42 is at a constant speed of rotation of 2200 r.p.m., for example, discharge pressure can be calculated based on the speed and the pump flow rate, in accordance with the characteristic shown in FIG. 5. In this case, speed control circuit 62 drives motor 32 such that the speed of motor 32 attains 2200 rpm, based on the instruction from CPU circuit 61. CPU circuit 61 provides indication of the speed at display 71, flow rate at display 72 and discharge pressure at display 73. In order to control the magnetic suspension type pump such that a prescribed flow rate is discharged, the pump flow rate is calculated based on the present speed and the motor driving current, which is compared with a preset flow rate, and feedback control is performed so that when the pump flow rate is lower, the speed is increased, and if it is higher, the speed is reduced. In operation with the discharge pressure kept constant, feedback control may be performed on the set pressure.

Figure 9:
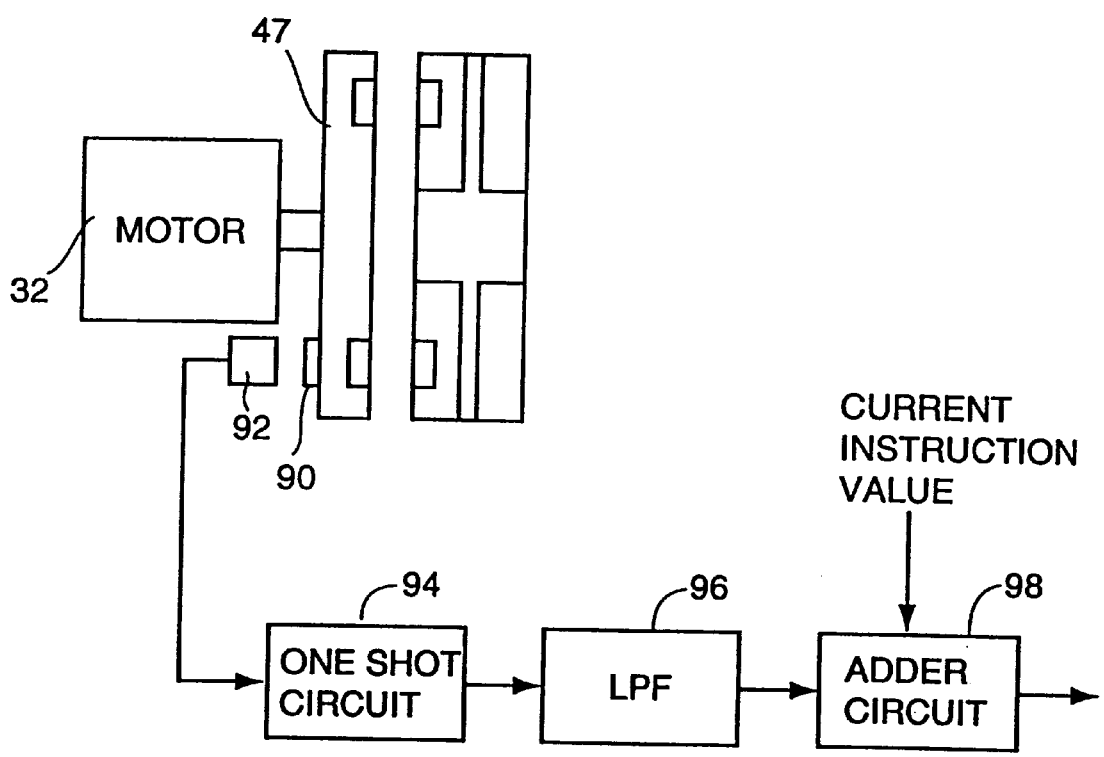
FIG. 9 is a diagram of one example of a speed feedback arrangement which may be used in the control scheme of FIG. 3.

FIG. 9 is a diagram of one example of a speed feedback arrangement which may be used in the control scheme of FIG. 3. Permanent magnet 90 is attached to rotor 47, which is driven by the motor 32, and a Hall generator element 92 is fixed in a housing, not shown, in close proximity to the permanent magnet 90. Rotational position of the motor rotor is detected by the Hall element 92, which generates an output pulse that is converted to a one shot pulse by a one shot circuit 94. The output of this circuit is passed to a low pass filter 96, from which an analog voltage proportional to the rotor speed is output. The speed thus can readily be determined from this voltage, which is input to adder circuit 98 and added to the current instruction value. The placement of magnet 90 may located on the impeller in lieu of the motor rotor. Such a feedback arrangement can be used for driving an induction motor as an alternative embodiment in the present invention.

Figure 6:
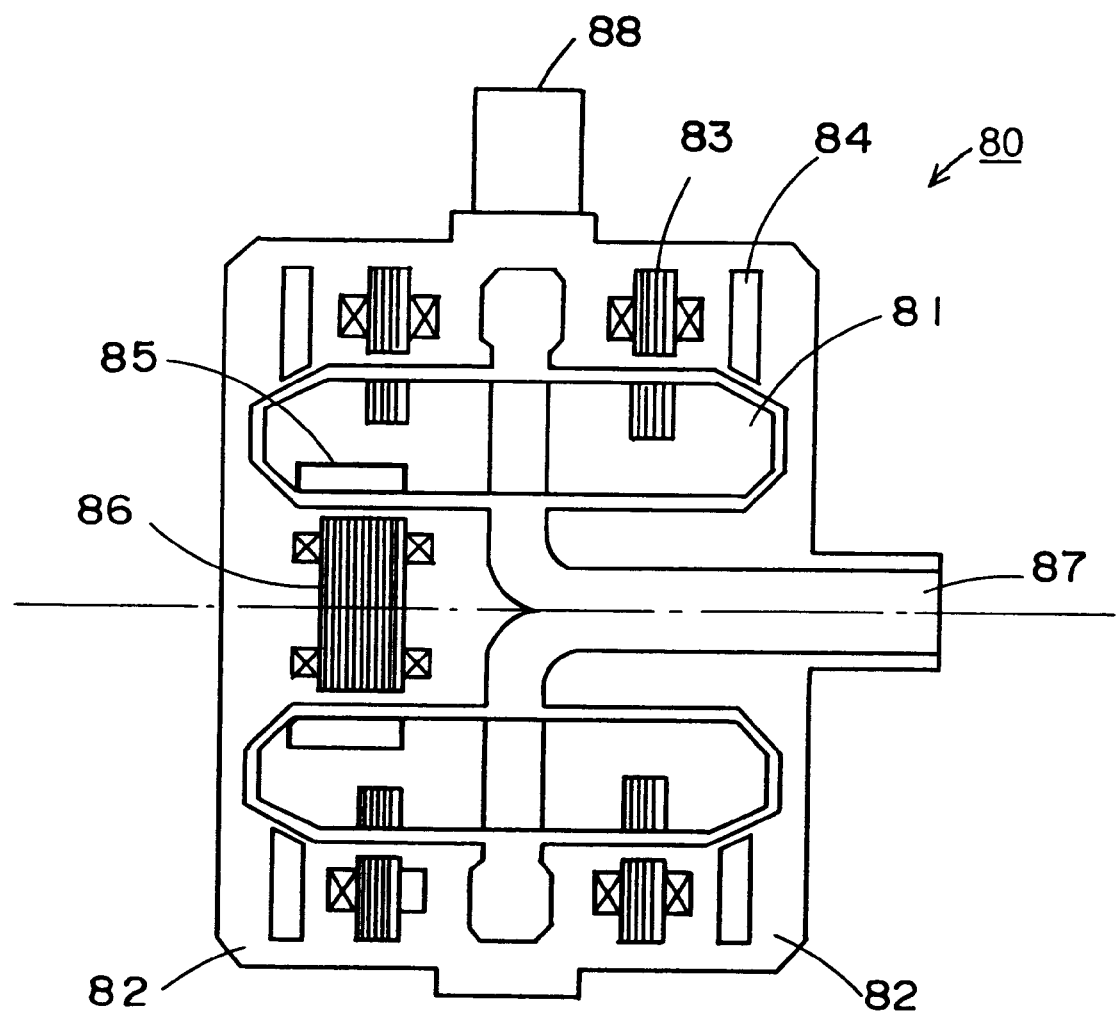
FIG. 6 shows another example of the magnetically suspended pump to which the present invention is applicable.
Figure 7:
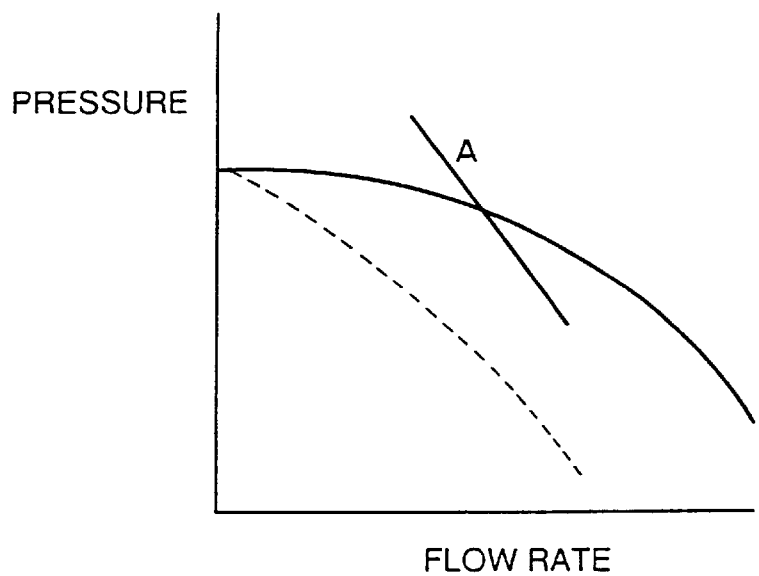
FIG. 7 shows flow rate-pressure characteristic of a typical centrifugal pump.
Figure 8:
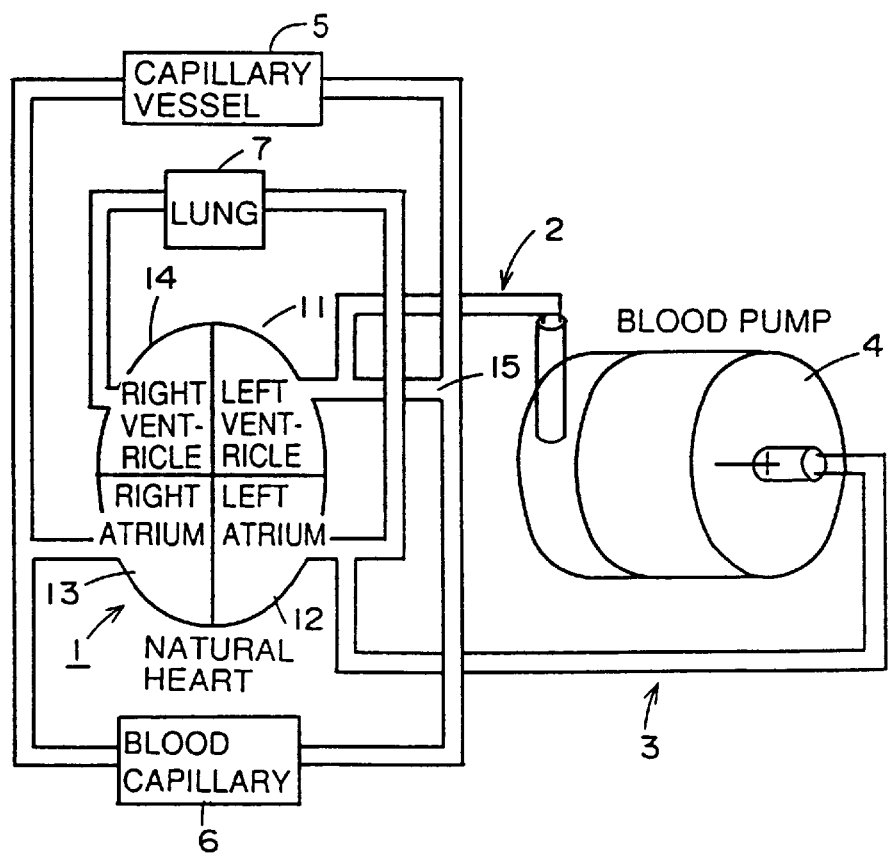
FIG. 8 shows an exemplary use of the blood pump for a natural heart bypass.

FIG. 6 shows another embodiment of a magnetic suspension type pump of the present invention is applied. Impeller 81 is supported by four axes of active control in the radial direction. Impeller 81 is actively supported by two radial magnetic bearings 82. Each radial magnetic bearing 82 includes an electromagnet 83 and a position sensor 84. Impeller 81 is provided with a permanent magnet 85. The permanent magnet 85 and a stator 86 provided opposing to the permanent magnet forms a DC brushless motor is provided to drive impeller 81 in rotation. Thus, blood is taken from inlet port 87 and discharged through outlet port 88.

As described above, according to the embodiments of the present invention, the current flowing through the motor for driving the blood pump is controlled to have a constant value. Therefore, variation in the flow rate of the blood pump can be suppressed with respect to the fluctuation of the pressure load. Further, an ideal pump characteristic can be obtained by adjusting positive feedback gain, and as the control circuit is implemented by analog circuitry, risk of malfunction can be reduced as compared with software processing.

Although the present invention has been described and illustrated in detail, it is clearly understood that the same is by way of illustration and example only and is not to be taken by way of limitation, the spirit and scope of the present invention being limited only by the terms of the appended claims.

What is claimed:

1. A method of controlling a blood pump for assisting or totally displacing a natural heart by bypass connection, said pump being in structural engagement with an electric motor to be driven thereby, said method comprising the steps of:

setting a current instruction value for said motor;

detecting motor current;

comparing said current instruction value with the detected motor current;

controlling the motor in response to said comparing step to maintain the motor current at said current instruction value;

sensing motor speed; and changing said current instruction value in response to the sensed motor speed.

2. A method as recited in claim 1, wherein said steps are performed by an analog circuit.

3. A method a recited in claim 1, further comprising the steps of:

detecting a viscosity value of blood flowing through said pump;

comparing the value of viscosity detected in said detecting step with a reference viscosity value;

determining a correction value in response to the step of comparing viscosity; and adding the correction value to said current instruction value.

4. A method as recited in claim 1, wherein said blood pump includes an impeller supported by a magnetic coupling, said impeller being driven by said motor through said magnetic coupling.

5. A method as recited in claim 4, wherein said magnetic coupling includes a first magnetic bearing supporting one side of said impeller and a second magnetic bearing supporting another side of said impeller.

6. A method as recited in claim 1, wherein said step of changing said current instruction value comprises adding positive speed feedback.

7. Apparatus for displacing a natural heart by a bypass connection, said apparatus comprising:

a blood pump;

a motor structurally coupled to said blood pump for driving said blood pump;

setting means for setting a current instruction value for said motor;

motor current detecting means for detecting motor current;

current comparison means for comparing said current instruction value with the detected motor current;

control means for controlling the motor in response to said comparing step to maintain the motor current at said current instruction value; and speed sensing means for sensing motor speed;

wherein said current instruction value is changed in response to the sensed motor speed.

8. Apparatus as recited in claim 7, further comprising:

viscosity detecting means for detecting viscosity of blood flowing through said pump;

viscosity comparison means for comparing a value of viscosity detected with a reference viscosity value;

correction means for determining a correction value in response to said viscosity comparison means; and adding means for adding the correction value to said current instruction value.

9. Apparatus as recited in claim 7, wherein said blood pump comprises an impeller supported by a magnetic coupling, wherein said impeller is driven by said motor through said magnetic coupling.

10. Apparatus as recited in claim 9, wherein said magnetic coupling includes a first magnetic bearing supporting one side of said impeller and a second magnetic bearing supporting another side of said impeller.

* * * * *